United States Patent
Shibuya et al.

(10) Patent No.: US 10,605,726 B2
(45) Date of Patent: Mar. 31, 2020

(54) ANALYSIS APPARATUS, PROGRAM FOR ANALYSIS APPARATUS, AND ANALYSIS METHOD

(71) Applicant: HORIBA, Ltd., Kyoto (JP)

(72) Inventors: Kyoji Shibuya, Kyoto (JP); Kensuke Fukushiro, Kyoto (JP); Toshio Ohta, Kyoto (JP); Katsumi Nishimura, Kyoto (JP)

(73) Assignee: HORIBA, LTD., Kyoto (JP)

( * ) Notice: Subject to any disclaimer, the term of this patent is extended or adjusted under 35 U.S.C. 154(b) by 26 days.

(21) Appl. No.: 15/827,542

(22) Filed: Nov. 30, 2017

(65) Prior Publication Data

US 2018/0172581 A1    Jun. 21, 2018

(30) Foreign Application Priority Data

Dec. 15, 2016   (JP) .................. 2016-243752

(51) Int. Cl.
*G01J 3/10*    (2006.01)
*G01N 21/39*   (2006.01)
(Continued)

(52) U.S. Cl.
CPC .............. *G01N 21/39* (2013.01); *G01J 3/433* (2013.01); *G01J 3/4338* (2013.01);
(Continued)

(58) Field of Classification Search
CPC .............. G01N 21/39; G01N 21/3504; G01N 2021/399; G01J 3/433; G01J 3/4338
(Continued)

(56) References Cited

U.S. PATENT DOCUMENTS 4,646,748 A * 3/1987 Fujii .................. A61B 8/14
600/441
6,356,350 B1   3/2002 Silver et al.
(Continued)

FOREIGN PATENT DOCUMENTS

JP   64-009342 A   1/1989
JP   02-069639 A   3/1990
(Continued)

OTHER PUBLICATIONS

EESR dated Apr. 5, 2018 issued for European patent application No. EP17204301.0; dated Apr. 5, 2018; 13 pages.
(Continued)

*Primary Examiner* — Isiaka O Akanbi
(74) *Attorney, Agent, or Firm* — Brooks Kushman P.C.

(57) ABSTRACT

The present invention is adapted to include: a light source adapted to emit reference light that is light whose wavelength is modulated at a predetermined modulation frequency; a light detector adapted to detect the intensity of measurement target light that is light after the reference light has transmitted through the measurement target component, and the intensity of the reference light; a first calculation part adapted to calculate an intensity ratio logarithm that is the logarithm of the ratio between the intensity of the measurement target light and the intensity of the reference light; a frequency component extraction part adapted to lock-in detect the intensity ratio logarithm with a reference signal having a frequency n times the modulation frequency; and a second calculation part adapted to, on the basis of the result of the detection by the frequency component extraction part, calculate the concentration or absorbance of the measurement target component.

20 Claims, 11 Drawing Sheets

(51) Int. Cl.
*G01J 3/433* (2006.01)
*G01N 21/3504* (2014.01)

(52) U.S. Cl.
CPC .... *G01N 21/3504* (2013.01); *G01J 2003/104* (2013.01); *G01N 2021/399* (2013.01)

(58) Field of Classification Search
USPC ................ 356/437, 436, 318–319, 409, 364
See application file for complete search history.

(56) References Cited

U.S. PATENT DOCUMENTS

| | | | | |
|---|---|---|---|---|
| 6,542,246 B1* | 4/2003 | Toida | ................... | A61B 5/0059 356/484 |
| 6,980,285 B1* | 12/2005 | Hansen | ..................... | G01J 3/28 356/319 |
| 7,782,460 B2* | 8/2010 | DiFoggio | ............... | G01N 21/31 250/263 |
| 8,352,008 B2* | 1/2013 | Kuhn | ................... | A61B 5/1495 600/336 |
| 2001/0006819 A1* | 7/2001 | Kawamura | ............ | G01N 21/82 436/86 |
| 2007/0024946 A1* | 2/2007 | Panasyuk | ............ | A61B 5/0059 359/253 |
| 2008/0081325 A1* | 4/2008 | Mannheimer | ...... | A61B 5/14551 435/4 |
| 2010/0091278 A1 | 4/2010 | Liu et al. | | |
| 2011/0276276 A1* | 11/2011 | Kashyap | .............. | G01N 21/474 702/19 |
| 2014/0340684 A1 | 11/2014 | Edler et al. | | |

FOREIGN PATENT DOCUMENTS

| | | |
|---|---|---|
| JP | 2009047677 A | 3/2009 |
| JP | 2009-222526 A | 10/2009 |
| JP | 2012-505405 A | 3/2012 |
| JP | 2012-173176 A | 9/2012 |
| JP | 2016-024156 A | 2/2016 |
| WO | 2010-042301 A2 | 4/2010 |

OTHER PUBLICATIONS

Menglong Cong et al, "Detection of NH3 using logarithmic-transformed wavelength modulation spectroscopy", Proceedings optical diagnostics of living cells II, Oct. 1, 2016, pp. 102552L-1 to 102552L-6, vol. 10255.

Zhirong Zhang et al, "Simultaneous detection of multiple gas concentrations with multi-frequency wavelength modulation spectroscopy" A Letters Journal Exploring the Frontiers of Physics, Nov. 1, 2013, pp. 44002-p1 to 14002-p6, vol. 104, No. 4.

Rubin Qi et al, "Wavelength modulation spectroscopy based on quasicontinuous-wave diode lasers" Chinese Optics Letters, Nov. 18, 2011, pp. 033001-1 to 033001-4, vol. 10, No. 3.

Haiwen Cai et al, "Fiber optic methane sensing system based on wavelength modulation spectroscopy by using logarithm method", Lasers and Electro-Optics-Pacific Rim 2007. CLEO/Pacific Rim 2007. Conference on, Aug. 1, 2007, 2 Pages.

Office Action dated Aug. 21, 2018 issued for Japanese Patent Application No. 2017-193620, 13 pgs.

Office Action dated Oct. 2, 2018 issued for Japanese Patent Application No. 2017-193620, 11 pgs.

* cited by examiner

ANALYSIS APPARATUS, PROGRAM FOR ANALYSIS APPARATUS, AND ANALYSIS METHOD

CROSS-REFERENCE TO RELATED APPLICATION

This application claims priority to Japanese Application No. 2016-243752, filed Dec. 15, 2016, the disclosure of which is incorporated in its entirety by reference herein.

TECHNICAL FIELD

The present invention relates to an analysis apparatus and the like used for analysis such as gas component analysis.

BACKGROUND ART

As an analysis method (TDLAS: Tunable Diode Laser Absorption Spectroscopy) adapted to sweep an oscillation wavelength by modulating the injection current of a semiconductor laser, and obtain the absorption spectrum of measurement target gas to quantify concentration, a wavelength modulation method (WMS: Wavelength Modulation Spectroscopy) adapted to apply current modulation having a small amplitude at a frequency sufficiently higher than a frequency used to modulate the current for the wavelength sweeping, and obtain the spectrum from a signal lock-in detected at a frequency twice the sufficiently higher frequency to quantify the concentration is often used in order to increase detection sensitivity.

For example, Patent Literature 1 discloses an example of a laser gas analyzer based on the wavelength modulation method (or also referred to as a frequency modulation method). In this example, the need for a reference gas cell for scanning the absorption wavelength of measurement target gas, i.e., for scanning the emission wavelength of a laser element is eliminated, and without stabilizing the emission wavelength to a specific wavelength, or without separately using a meter such as a dust meter even in a dusty environment, gas concentration can be accurately measured by correcting the amplitude of a gas absorption waveform using a received light amount correction coefficient.

CITATION LIST

Patent Literature

Patent Literature 1: Japanese Unexamined Patent Publication JP-A 2009-47677

SUMMARY OF INVENTION

Technical Problem

However, in a normal WMS, when the entire signal intensity uniformly varies due to the variation of laser intensity from that at the time of zero calibration, an indicated value varies, and that cause drift. In order to suppress the drift, as disclosed in Patent Literature 1 described above, it is necessary to monitor the laser intensity in some way to make a correction simultaneously.

Also, in the WMS, in order to quantify concentration from a spectrum obtained by wavelength sweeping, a spectrum calculation process (such as obtaining the difference between the maximum and minimum value within a specific range of the spectrum) is further required.

Further, in the WMS, for the lock-in detection, it is necessary to apply modulation at a frequency sufficiently higher than the modulation frequency for the wavelength sweeping, and in order to respond to such a high frequency signal, sufficient response speed is required for a detector as well. For a near-infrared region often used in the WMS, quantum detectors having sufficient response speed are relatively easily available at low cost; however, for a mid-infrared region preferable for gas analysis, quantum detectors having high response speed are mostly expensive, and it is difficult to perform the WMS using an inexpensive but low response speed thermal detector.

Still further, when part of a spectrum of a component other than a measurement target component is superposed on a spectrum obtained by the WMS, in order to remove the interference effect of it, complicated calculation processes such as spectrum fitting, baseline estimation, and multivariate analysis are required.

The present invention is made in consideration of the problems as described above, and a desired object thereof is to allow an analysis apparatus utilizing light absorption to accurately measure the absorbance or concentration of a measurement target component with simple calculation while eliminating some effects such as the effect of a variation in light source intensity and the effect of interference by another substance.

Solution to Problem

That is, the analysis apparatus according to the present invention is one adapted to analyze a measurement target component contained in a sample, and the analysis apparatus includes: a light source adapted to emit reference light that is light whose wavelength is modulated at a predetermined modulation frequency; a light detector adapted to detect the intensity of measurement target light that is light after the reference light has transmitted through the sample, and the intensity of the reference light; a first calculation part adapted to calculate an intensity ratio logarithm that is the logarithm of the ratio between the intensity of the measurement target light and the intensity of the reference light; a frequency component extraction part adapted to, from the intensity ratio logarithm, extract a frequency component having a frequency n times (n is an integer equal to or more than 1) the modulation frequency; and a second calculation part adapted to, on the basis of the result of the frequency component extraction by the frequency component extraction part, calculate the concentration or absorbance of the measurement target component.

In such a configuration, since the intensity ratio logarithm (hereinafter also referred to as an absorbance signal) that is the logarithm of the ratio between the intensity of the measurement target light and the intensity of the reference light is calculated before the extraction of the frequency component, for example, even when the entire signal intensity uniformly varies due to the variation of laser intensity from that at the time of zero calibration (at the time of measuring the intensity of the reference light), a measurement result is not affected. Therefore no drift occurs. Accordingly, the need to monitor the light source intensity for drift suppression simultaneously is eliminated.

Also, a value obtained by the frequency component extraction part is proportional to the value of the concentration of the measurement target component directly. As a result, the need for a spectrum calculation process for concentration quantification, which is required for WMS, can be eliminated, and only a single modulation frequency is required, leading to a simpler system configuration and low cost.

Further, since the frequency for extracting the component can be set equal to the modulation frequency or set to at most several times the modulation frequency, analysis accuracy equivalent to that of WMS can be obtained using a low response speed light detector not applicable to WMS. This effect remarkably appears in the mid-infrared region. This is because a light detector whose response speed is high in the mid-infrared region is relatively expensive, and therefore being able to use an inexpensive thermal detector is directly linked to being able to enjoy a big benefit in terms of cost.

Also, according to the present invention, even when the sample contains an interference component, the unconventional dramatic idea of converting such a problem into a linear problem based on logarithmic calculation and finally leading to a direct problem of solving simultaneous equations allows the concentration of the measurement target component to be surely measured. An example of a specific configuration for this is as follows.

That is, the frequency component extraction part is one adapted to, from the intensity ratio logarithm (absorbance signal) calculated by the first calculation part, extract mutually different frequency components whose number is equal to or more than the sum of the number of the measurement target component and the number of interference components, the analysis apparatus stores independent frequency components that are frequency components of absorbance signals when the measurement target component and the respective interference components are independently present or stores independent absorbance signals (independent intensity ratio logarithms) that are absorbance signals of the measurement target component and the respective interference components per unit concentration, and the second calculation part is one adapted to calculate the concentration of the measurement target component on the basis of the result of the frequency component extraction by the frequency component extraction part and the independent frequency components or the independent absorbance signals.

Specifically, it can be cited that the second calculation part is one adapted to calculate the concentration of the measurement target component by solving simultaneous equations including the result of the extraction of the respective frequency components by the frequency component extraction part, the independent frequency components or the independent intensity ratio logarithms of the measurement target component and the respective interference components, and the concentrations of the measurement target component and the respective interference components. In this configuration, simple and certain calculation, i.e., solving the simultaneously equations allows the concentration of the measurement target gas, from which an interference effect has been removed, to be determined.

In order to make it possible to determine the concentration with an error due to measurement noise being small, it is preferable that the frequency component extraction part is one adapted to extract frequency components whose number is larger than the sum of the number of the measurement target component and the number of the interference components, and the second calculation part is one adapted to calculate the concentration of the measurement target component with use of a least squares method from simultaneous equations where the number of unknowns is larger than the sum of the number of the measurement target component and the number of the interference components.

As the frequency component extraction part, one adapted to extract the frequency component or the frequency components by performing lock-in detection at the frequency n times (n is an integer equal to or more than 1) the modulation frequency can be cited.

As a specific method for calculating the intensity ratio logarithm by the first calculation part, for example, a method adapted to calculate the intensity ratio logarithm by obtaining the ratio between the intensity of the measurement target light and the intensity of the reference light and obtaining the logarithm of the ratio, or a method adapted to calculate the intensity ratio logarithm by obtaining the logarithm of the intensity of the measurement target light as well as obtaining the logarithm of the intensity of the reference light, and subtracting the logarithm of the intensity of the reference light from the logarithm of the intensity of the measurement target light can be cited.

The analysis apparatus of the present invention is applicable to analyzing gas or the like.

Specifically, it can be cited that the light source is a semiconductor laser adapted to emit the reference light modulated in a wavelength range including the peak wavelength of the light absorption spectrum of the measurement target component, the analysis apparatus further includes a gas cell into which the sample gas is introduced, the gas cell is irradiated with the reference light emitted from the semiconductor laser, and the light detector is arranged in the light path of the measurement target light having transmitted through the gas cell.

Also, it is preferable that the analysis apparatus further includes a light source control part adapted to make the light source operate in quasi-continuous-wave (quasi-CW) oscillation, and generate a temperature change based on current modulation to sweep an oscillation wavelength.

When a low response speed detector such as a thermopile detects pulse train signals, the wavelength modulation by the light source control part allows the pulse train signals to be averaged, and therefore the same result can be obtained as that obtained when making the light source operate in continuous-wave (CW) oscillation and using a high response speed light detector such as an MCT. In this case, as the pulse width of the quasi-CW oscillation is decreased, wavelength resolution increases, and as the duty ratio is increased, signal intensity increases. Also, as compared with the CW oscillation, the quasi-CW oscillation makes it possible to decrease the power consumption of the light source, facilitate waste heat disposal, and further prolong the life of the light source.

In addition, it is preferable that the analysis apparatus further includes a signal separation part adapted to, from a light intensity signal obtained by the light detector, separate a signal corresponding to a part of a pulse from the light source.

By separating a signal corresponding to a part of a pulse from the light source as described, the pulse width of the pulse does not directly affect wavelength resolution, and therefore a reduction in wavelength resolution can be suppressed without shortening the pulse width. As a result, as compared with a conventional quasi-CW oscillation method, the wavelength resolution can be significantly improved. In addition, since shortening the pulse width to prevent the reduction in wavelength resolution is not required, the technical difficulty required for electronics for driving the light source is reduced, and correspondingly, cost is also reduced.

When the semiconductor laser used as the light source operates in pulse oscillation, temperature changes to thereby change a wavelength. The degree of such a transient temperature change (wavelength change) becomes smaller toward the latter half of a pulse, and therefore by separating a signal corresponding to the latter half, the wavelength resolution is improved. For this reason, it is preferable that the signal separation part separates a signal corresponding to the latter half of a pulse of the light source. This configuration makes it possible to significantly improve the wavelength resolution as compared with the conventional quasi-CW oscillation method by relatively widening the pulse width of a pulse (e.g., approximately 100 ns) and setting a sampling position to a time position within the pulse as far back as possible (e.g., 85 to 95 ns after the rise of the pulse). In addition, the sampling is performed within a predetermined time width.

Advantageous Effects of Invention

According to the present invention described above, the analysis apparatus utilizing light absorption is capable of accurately measure the absorbance or concentration of a measurement target component while ensuring a simple and inexpensive configuration and eliminating effects such as the effect of a variation in light source intensity and the effect of interference by another substance.

DESCRIPTION OF EMBODIMENTS

In the following, an analysis apparatus 100 according to one embodiment of the present invention will be described with reference to the drawings.

Figure 1:
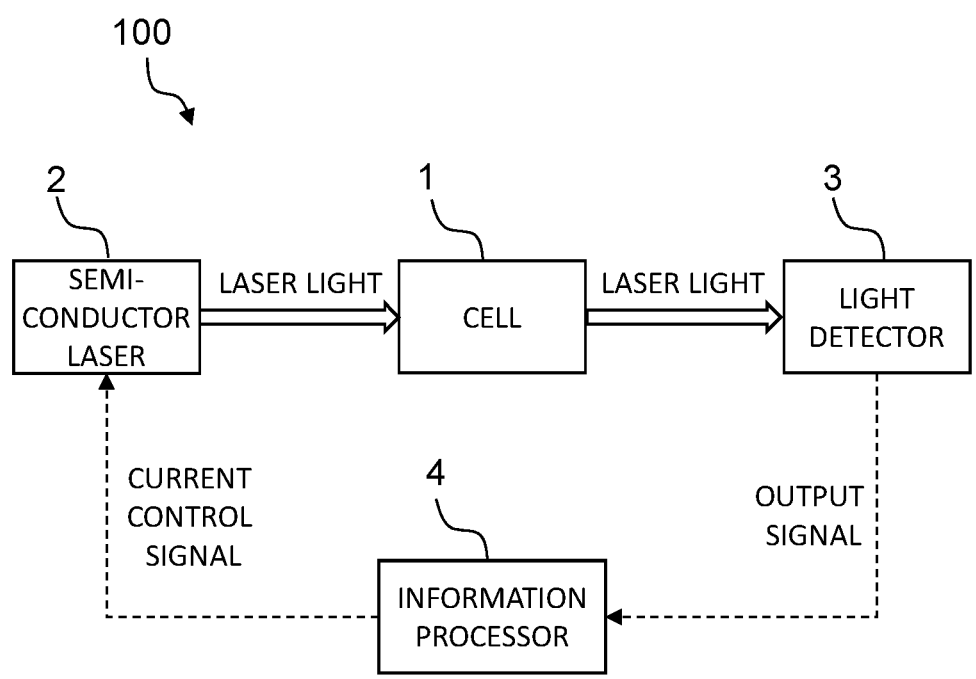
FIG. 1 is an overall schematic diagram of an analysis apparatus according to one embodiment of the present invention.

The analysis apparatus 100 is a concentration measurement apparatus adapted to measure the concentration of a measurement target component (such as CO or $CO_2$ herein) contained in sample gas such as exhaust gas, and as illustrated in FIG. 1, includes: a cell 1 into which the sample gas is introduced, a semiconductor laser 2 as a light source adapted to irradiate the cell 1 with laser light; a light detector 3 adapted to be provided in the light path of laser light having transmitted through the cell 1 and receive the laser light; and an information processor 4 adapted to receive an output signal from the light detector 3 and on the basis of the value of the output signal, calculate the concentration of the measurement target component.

The respective parts will be described.

The cell 1 is one whose light incident and exit ports are formed of a transparent material hardly absorbing light in the absorption wavelength band of the measurement target component, such as quartz, calcium fluoride, or barium fluoride. Although not illustrated in FIG. 1, the cell 1 is provided with an inlet port for introducing gas inside and an outlet port for exhausting internal gas, and the sample gas is introduced into the cell 1 through the inlet port and then enclosed.

The semiconductor laser 2 is a quantum cascade laser (QCL) herein, a type of a semiconductor laser 2, and oscillates laser light in the mid-infrared region (4 μm to 10 μm). The semiconductor laser 2 is capable of modulate (change) an oscillation wavelength depending on a given current (or voltage). Note that as long as an oscillation wavelength is variable, another type of laser may be used, and in order to change an oscillation wavelength, some means may be taken, such as changing temperature.

As the light detector 3, a relatively inexpensive thermal type such as a thermopile is used herein; however, another type, for example, a highly responsive quantum photoelectric element such as one using HgCdTe, InGaAs, InAsSb, or PbSe may be used.

Figure 2:
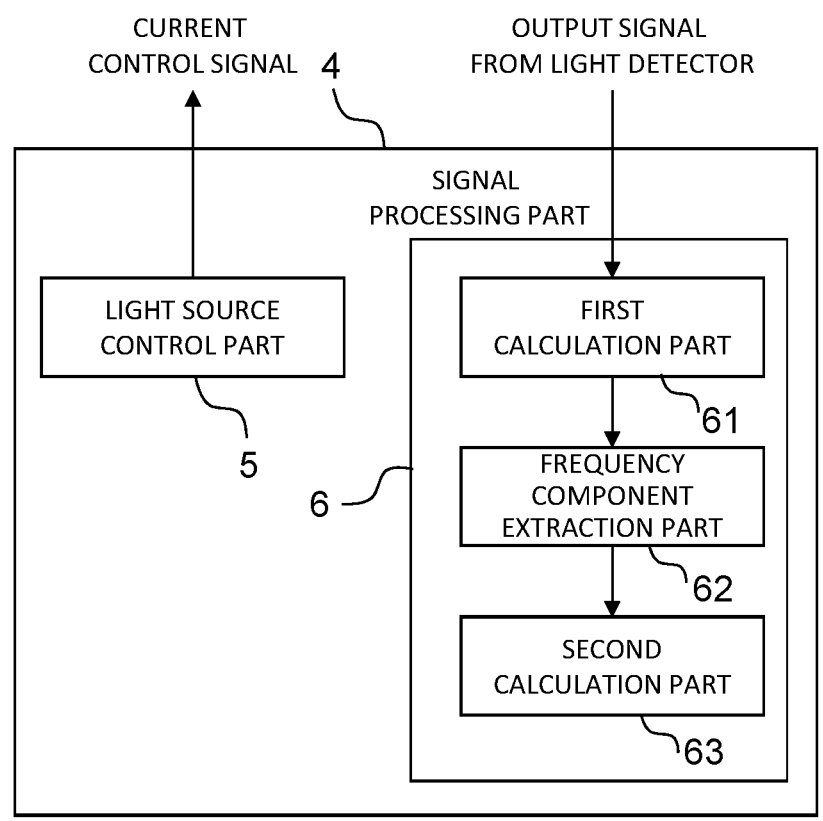
FIG. 2 is a functional block diagram of an information processor in the same embodiment.

The information processor 4 is one including: an analog electric circuit including a buffer, an amplifier, and the like; a digital electric circuit including a CPU, a memory, and the like; AD and DA converters acting as interfaces between the analog and digital electric circuits; and the like. In addition, the CPU and its peripheral devices cooperate in accordance with a predetermined program stored in a predetermined area of the memory, and thereby as illustrated in FIG. 2, the information processor 4 fulfills functions as a light source control part 5 adapted to control the output of the semiconductor laser 2 and a signal processing part 6 adapted to receive an output signal from the light detector 3 and perform a calculation process on the value of the output signal to calculate the concentration of the measurement target component.

The respective parts will be described below in detail.

The light source control part 5 is one adapted to output a current (voltage) control signal and thereby control the current source (or the voltage source) of the semiconductor laser 2, and this allows the drive current (or the drive voltage) of the semiconductor laser 2 to be changed at a predetermined frequency, therefore modulating the oscillation wavelength of the laser light outputted from the semiconductor laser 2 at the predetermined frequency.

Figure 3:
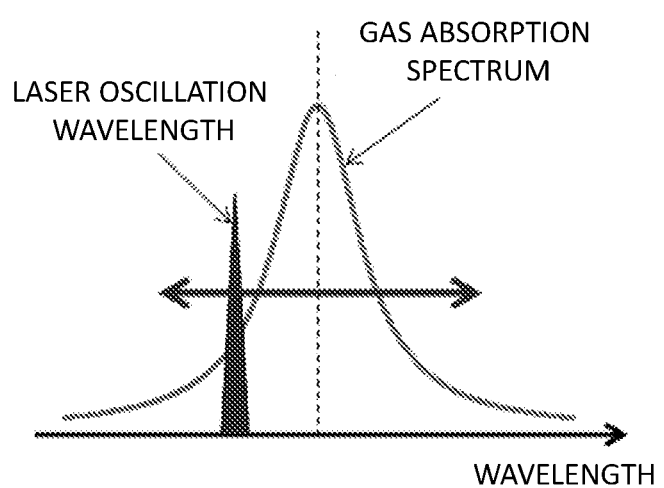
FIG. 3 is a schematic diagram illustrating a method for modulating a laser oscillation wavelength in the same embodiment.
Figure 4:
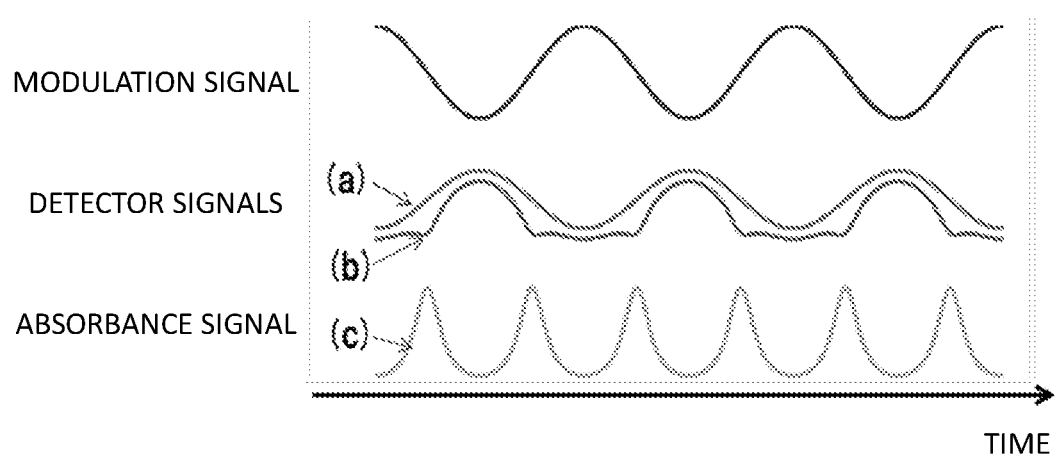
FIG. 4 is a time-series graph illustrating an example of a modulation signal, output signals from a light detector, and a measurement result in the same embodiment.

In this embodiment, the light source control part 5 changes the drive current into a sine wave shape, and modulates the oscillation frequency into a sine wave shape (see a modulation signal in FIG. 4). Also, as illustrated in FIG. 3, the oscillation frequency of the laser light is adapted to be modulated with the peak of the light absorption spectrum of the measurement target component as a center.

The signal processing part 6 includes a first calculation part 61, a frequency component extraction part 62, a second calculation part 63, and the like.

The first calculation part 61 is one adapted to calculate the logarithm of the ratio (hereinafter also referred to as an intensity ratio logarithm) between the light intensity of the laser light (hereinafter also referred to as measurement target light) having transmitted through the cell 1 in a state where the sample gas is enclosed and light is absorbed by the measurement target component of the sample gas and the light intensity of laser light (hereinafter also referred to as reference light) having transmitted through the cell 1 in a state where light absorption is substantially zero.

Describing more specifically, both of the former and latter light intensities are measured by the light detector 3, the resulting pieces of measurement result data are stored in a predetermined area of the memory, and the first calculation part 61 refers to the pieces of measurement result data to calculate the intensity ratio logarithm.

In addition, the former measurement (hereinafter also referred to as sample measurement) is of course performed on every sample gas. The latter measurement (hereinafter also referred to as reference measurement) may be performed any of before and after every sample measurement, or may be performed, for example, once at appropriate timing, and the result of the measurement may be stored in the memory and used in common for every sample measurement.

Note that in this embodiment, in order to obtain the state where light absorption is substantially zero, zero gas whose light absorption is substantially zero in a wavelength band where the measurement target component absorbs light, for example, $N_2$ gas is enclosed in the cell 1; however, another gas may be enclosed, or the cell 1 may be evacuated.

The frequency component extraction part 62 is one adapted to lock-in detect the intensity ratio logarithm (hereinafter also referred to as an absorbance signal) calculated by the first calculation part 61 with a reference signal having a frequency n times (n is an integer equal to or more than 1) the modulation frequency, and extract a frequency component having the frequency of the reference signal from the intensity ratio logarithm. Note that the lock-in detection may be performed by digital calculation or by calculation through an analog circuit. Also, the frequency component may be extracted using not only the lock-in detection but also a method such as Fourier series expansion.

The second calculation part 63 is one adapted to, on the basis of the result of the detection by the frequency component extraction part 62, calculate the concentration of the measurement target component.

Next, an example of the operation of the analysis apparatus 100 will be described while describing the respective parts above in detail.

First, as described above, the light source control part 5 controls the semiconductor laser 2 to modulate the wavelength of the laser light at the modulation frequency with the peak of the absorption spectrum of the measurement target component as a center.

Then, when zero gas is enclosed in the cell 1 by an operator or automatically, the first calculation part 61 having sensed the enclosure performs the reference measurement.

Specifically, the first calculation part 61 receives an output signal from the light detector 3 in a state where the zero gas is enclosed in the cell 1, and stores the value of the output signal in a measurement result data storage part. When displaying the value of the output signal from the light detector 3 in the reference measurement, i.e., reference light intensity in a time-series graph, a curve as illustrated in (a) of FIG. 4 is obtained. That is, only a change in light output caused by the modulation of the laser drive current (voltage) is displayed as the output signal from the light detector 3.

Subsequently, when the sample gas is enclosed in the cell 1 by the operator or automatically, the first calculation part 61 performs the sample measurement. Specifically, the first calculation part 61 receives an output signal from the light detector 3 in a state where the sample gas is enclosed in the cell 1, and stores the value of the output signal in a predetermined area of the memory. When displaying the value of the output signal from the light detector 3 in the sample measurement, i.e., measurement target light intensity in the time-series graph, a curve as illustrated in (b) of FIG. 4 is obtained. It turns out that an absorption peak appears in every half period of the modulation.

After that, the first calculation part 61 synchronizes respective pieces of measurement data with the modulation period, and calculates the intensity ratio logarithm between the light intensity of the measurement target light and the light intensity of the reference light. Specifically, the first calculation part 61 performs the calculation in accordance with the following expression (Expression 1).

$$A(t) = -\ln\left(\frac{D_m(t)}{D_z(t)}\right) \qquad \text{[Expression 1]}$$

Here, $D_m(t)$ represents the measurement target light intensity, $D_z(t)$ the reference light intensity, and $A(t)$ the intensity ratio logarithm (absorbance signal). When displaying the absorbance signal in the graph with the horizontal axis as time, a curve as illustrated in (c) of FIG. 4 is obtained.

The intensity ratio logarithm calculation may be performed by calculating the ratio between the measurement target light intensity and the reference light intensity and then obtaining the logarithm of the ratio, or obtaining the logarithm of the measurement target light intensity and the logarithm of the reference light intensity, and then obtaining the difference between them.

Then, the frequency component extraction part 62 lock-in detects the intensity ratio logarithm with the reference signal having the frequency twice the modulation frequency, i.e., extracts the frequency component having the frequency twice the modulation frequency, and stores the resulting data (hereinafter also referred to as lock-in data) in a predetermined area of the memory.

The value of the lock-in data is a value proportional to the concentration of the measurement target component, and the second calculation part 63 calculates, on the basis of the value of the lock-in data, a concentration indicated value indicating the concentration of the measurement target component.

In such a configuration, even when laser light intensity varies due to some cause, a constant offset is only added to the above-described intensity ratio logarithm but a waveform does not change. Accordingly, the value of each frequency component calculated by lock-in detecting the intensity ratio logarithm added with the constant offset does not change, and a concentration indicated value also does not change, therefore making it possible to expect accurate measurement.

Describing the reason for this in detail, it is as follows.

In general, when expanding the absorbance signal $A(t)$ into a Fourier series, it is expressed by the following expression (Expression 2).

In addition, in the expression (Expression 2), $a_n$ represents a value proportional to the concentration of the measurement target component, and on the basis of the value $a_n$, the second calculation part 63 calculates the concentration indicated value indicating the concentration of the measurement target component.

$$A(t) = a_0 + \sum_{n=1}^{\infty} a_n \cos(2\pi n f_m t + \phi_n) \qquad \text{[Expression 2]}$$

Here, $f_m$ represents the modulation frequency, and n represents a multiple of the modulation frequency.

On the other hand, A(t) is also expressed by the above expression (Expression 1).

Next, an absorbance signal A'(t) obtained when the laser light intensity varies a times due to some cause during the measurement is expressed as the following expression (Expression 3).

$$A'(t) = -\ln\left(\frac{\alpha D_m(t)}{D_z(t)}\right) = -\ln\left(\frac{D_m(t)}{D_z(t)}\right) - \ln(\alpha) = A(t) - \ln(\alpha) \qquad \text{[Expression 3]}$$

As is clear from this expression (Expression 3), A'(t) is equal to the absorption signal A(t), which is a signal in the absence of a variation in the laser light intensity, only added with $-\ln(\alpha)$ as a constant value, and therefore it turns out that even when the laser light intensity changes, the value $a_n$ of each frequency component does not change.

Accordingly, the concentration indicated value determined on the basis of the value of the frequency component having the frequency twice the modulation frequency is not affected.

The above is the example of the operation of the analysis apparatus 100 at the time when the sample gas does not contain an interference component other than the measurement target component.

Next, an example of the operation of the present analysis apparatus 100 at the time when at least one interference component (e.g., $H_2O$) absorbing light at the peak light absorption wavelength of the measurement target component is contained in the sample gas will be described.

First, a principle will be described.

Since the light absorption spectrum of the measurement target component and the light absorption spectrum of the interference component are different in shape, absorbance signals obtained when the respective components are independently present are different in waveform, and therefore the ratios of respective frequency components are different (linearly independent). By utilizing this and solving simultaneous equation using the relationship between the values of respective frequency components of measured absorption signals and preliminarily obtained respective frequency components of absorbance signals of the measurement target component and the interference component, the concentration of the measurement target component, from which the interference effect has been corrected, can be obtained.

Given that absorbance signals per unit density obtained when the measurement target component and the interference component are independently present are respectively represented by $A_m(t)$ and $A_i(t)$, and respective frequency components of the absorbance signals are represented by $a_{nm}$ and $a_{ni}$, the following expressions (Expressions 4 and 5) hold.

$$A_m(t) = a_{0m} + \sum_{n=1}^{\infty} a_{nm} \cos(2\pi n f_m t + \phi_n) \qquad \text{[Expression 4]}$$

$$A_i(t) = a_{0i} + \sum_{n=1}^{\infty} a_{ni} \cos(2\pi n f_m t + \phi_n) \qquad \text{[Expression 5]}$$

An absorbance signal value A(t) obtained when the measurement target component and the interference component are present at concentrations of $C_m$ and $C_i$, respectively is expressed by the following expression (Expression 6) on the basis of the linearities of the respective absorbances.

$$\begin{aligned} A(t) &= C_m A_m(t) + C_i A_i(t) \\ &= C_m \left( a_{0m} + \sum_{n=1}^{\infty} a_{nm} \cos(2\pi n f_m t + \phi_n) \right) + \\ &\quad C_i \left( a_{0i} + \sum_{n=1}^{\infty} a_{ni} \cos(2\pi n f_m t + \phi_n) \right) \\ &= a_{0m} C_m + a_{0i} C_i + \sum_{n=1}^{\infty} (a_{nm} C_m + a_{ni} C_i) \cos(2\pi n f_m t + \phi_n) \end{aligned} \qquad \text{[Expresssion 6]}$$

Given here that frequency components of A(t) at $f_m$ and $2f_m$ are respectively represented by $a_1$ and $a_2$, the following simultaneous equations (Expression 7) hold from the above expression (Expression 6).

$$a_{1m} C_m + a_{1i} C_i = a_1$$
$$a_{2m} C_m + a_{2i} C_i = a_2 \qquad \text{[Expression 7]}$$

The frequency components $a_{nm}$ and $a_{ni}$ (n is a natural number and n=1, 2 herein) respectively obtained when the measurement target component and the interference component are independently present can be preliminarily obtained by flowing corresponding span gases, and therefore simple and certain calculation, i.e., solving the above simultaneous equations (Expression 7) allows the concentration $C_m$ of the measurement target gas, from which the interference effect has been eliminated, to be determined.

The analysis apparatus 100 operates on the basis of the above-described principle.

That is, the analysis apparatus 100 in this case stores, in a predetermined area of the memory, the frequency components $a_{1m}$, $a_{2m}$, $a_{1i}$, and $a_{2i}$ (independent frequency components in claims) of the absorbance signals obtained by some means such as preliminarily make measurements while flowing corresponding span gases when the measurement target component and the interference component are independently present. Specifically, as in the above example, for each of the measurement target component and the interference component, the measurement target light intensity and the reference light intensity are measured to calculate the intensity ratio logarithm (absorbance signal) between them, and from the intensity ratio logarithm, the frequency components $a_{1m}$, $a_{2m}$, $a_{1i}$, and $a_{2i}$ are obtained by the lock-in detection or another means and then stored. Note that it may be adapted not to store the frequency components but to store the absorbance signals per unit concentration $A_m(t)$ and $A_i(t)$ (independent logarithmic intensity ratios in claims), and calculate the frequency components $a_{1m}$, $a_{2m}$, $a_{1i}$, and $a_{2i}$ from the above expression (Expression 4).

Then, the analysis apparatus 100 specifies the measurement target component and the interference component by inputs from an operator or the like.

Subsequently, the first calculation part 61 calculates the intensity ratio logarithm $A(t)$ in accordance with the above expression (Expression 1).

After that, the frequency component extraction part 62 lock-in detects the intensity ratio logarithm with reference signals respectively having the modulation frequency $f_m$ and the frequency $2f_m$ twice the modulation frequency $f_m$ to extract the respective frequency components $a_1$ and $a_2$ (pieces of lock-in data), and stores them in the predetermined area of the memory.

Then, the second calculation part 63 substitutes the values of the pieces of lock-in data $a_1$ and $a_2$ and the values of the frequency components $a_{1m}$, $a_{2m}$, $a_{1i}$, and $a_{2i}$ stored in the memory into the above-expression (Expression 7), or performs equivalent calculation to calculate concentration (or a concentration indicated value) $C_m$ indicating the concentration of the measurement target gas, from which the interference effect has been removed. At this time, the concentration (concentration indicated value) $C_i$ of each interference component may be calculated.

Note that even when two or more interference components can be assumed to be present, by adding higher order frequency components whose number corresponds to the number of the interference components and solving simultaneous equations where the number of unknowns is equal to the number of components, the concentration of the measurement target component, from which the interference effect has been removed, can be determined.

That is, in general, when the total number of a measurement target component and interference components existing is n, given that the frequency component of the k-th gas component at $i \times f_m$ is represented by $a_{ik}$, and the concentration of the k-th gas component is represented by $C_k$, the following expression (Expression 8) holds.

$$a_{11}C_1 + a_{12}C_2 + a_{13}C_3 + \ldots + a_{1n}C_n = a_1 \quad \text{[Expression 8]}$$
$$a_{21}C_1 + a_{22}C_2 + a_{23}C_3 + \ldots + a_{2n}C_n = a_2$$
$$a_{31}C_1 + a_{32}C_2 + a_{33}C_3 + \ldots + a_{3n}C_n = a_3$$
$$\vdots$$
$$a_{n1}C_1 + a_{n2}C_2 + a_{n3}C_3 + \ldots + a_{nn}C_n = a_n$$

By solving the simultaneous equations with n unknowns expressed by this expression (Expression 8), the concentrations of the measurement target component and the interference components can be determined.

Also, it may be adapted to add a higher harmonic component of an order higher than n to prepare simultaneous equations where the number of equations is larger than the number of gas components, and determine the concentrations of the respective components using the least squares method. In doing so, the concentrations can be determined with errors due to measurement noise being small.

Note that when the total number of a measurement target component and interference components is n, the concentrations of the respective components are calculated, and there are some components whose concentrations are equal to or less than a predetermined threshold value, it is conceivable to recalculate the concentrations of components other than the components having concentrations equal to or less than the threshold value.

Figure 5:
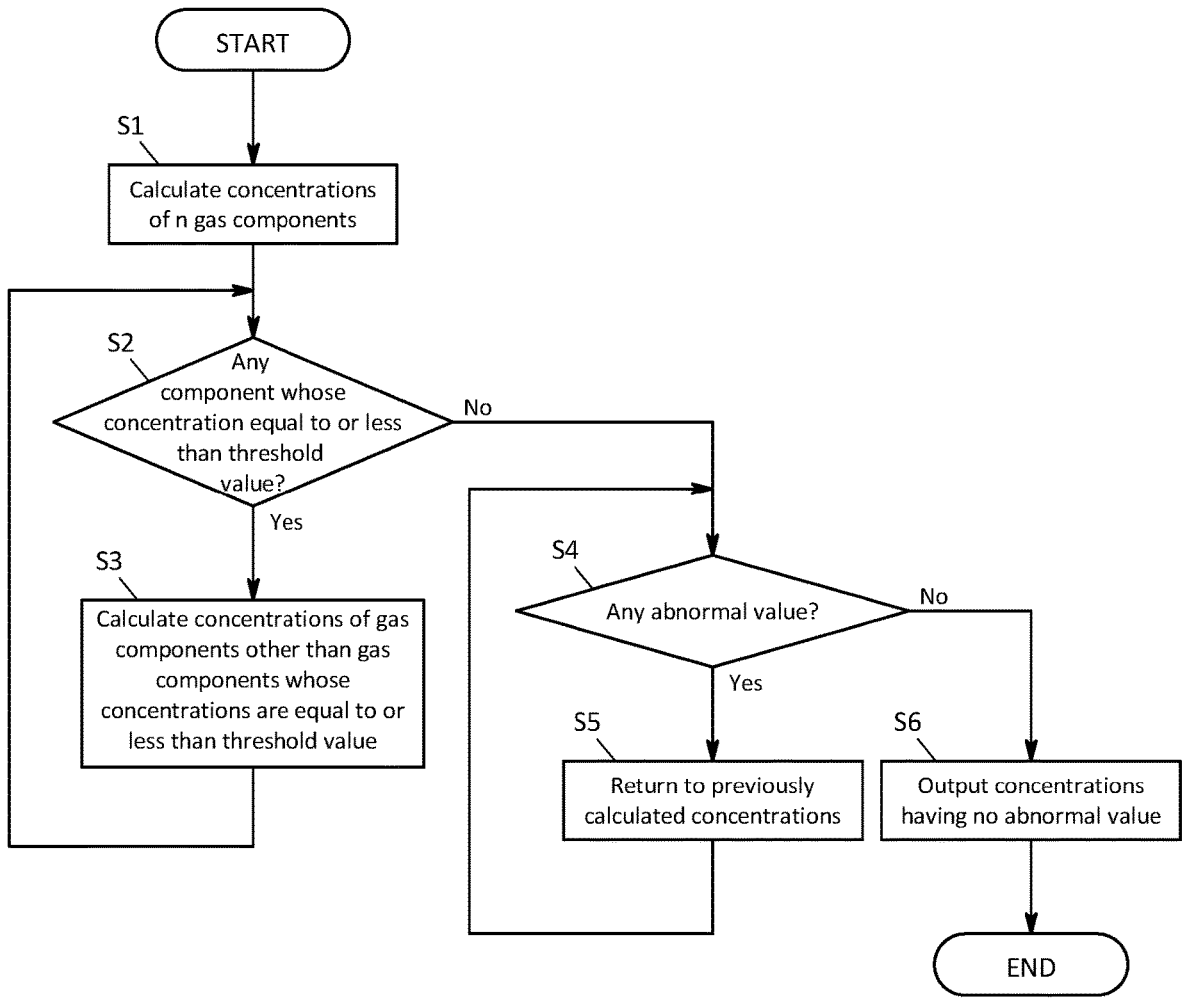
FIG. 5 is a flowchart illustrating concentration calculation in a variation.

Specifically, as illustrated in FIG. 5, the second calculation part 63 solves the simultaneous equations with n unknowns expressed by the above expression (Expression 8) to calculate the concentrations of the n components (S1). Then, a determination part provided in the signal processing part 6 determines whether or not there is any component whose component is equal to or less than the predetermined threshold value (S2). When there are j components whose concentrations are equal to or less than the threshold value, the second calculation part 63 recalculates the concentrations of (n−j) components other than the j components whose concentrations are equal to or less than the threshold value using simultaneous equations with (n−j) unknowns expressed on the basis of the same idea as for the above expression (Expression 8) (S3). This makes it possible to accurately calculate the concentrations of the existing gas components. The above series of calculation is repeated until no component whose concentration is equal to or less than the threshold value is detected, or the concentration of the measurement target component is repeatedly calculated a predetermined number of times.

In addition, as operation after it has been determined that no component whose concentration is equal to or less than the threshold value is left, for example, an embodiment adapted to determine whether or not any of calculated concentrations has an abnormal value can be cited (S4). In S4, when there is an abnormal value, the second calculation part 63 checks previously calculated concentrations (S5) to determine whether or not any of the previously calculated concentration has an abnormal value. On the other hand, in S4, when there is no abnormal value, the concentrations not exhibiting any abnormal value are outputted (S6).

Note that the present invention is not limited to the above-described embodiment.

Figure 6:
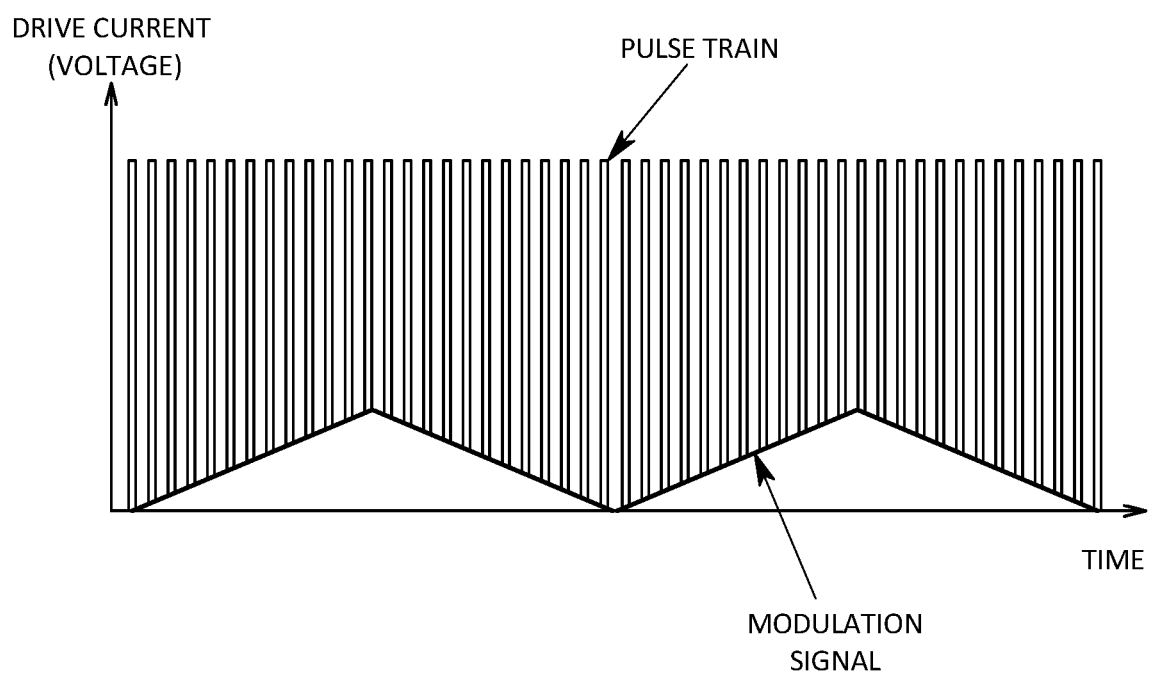
FIG. 6 is a diagram illustrating drive current (voltage) and a modulation signal in quasi-CW oscillation.

For example, the light source control part 5 in the above-described embodiment is one adapted to make the semiconductor laser operate in CW oscillation, but as illustrated in FIG. 6, may be one adapted to make the semiconductor laser operate in quasi-CW oscillation. In this case, the light source control part 5 outputs the current (or voltage) control signal to thereby control the current source (or the voltage source) for the semiconductor laser 2, and sets the drive current (the drive voltage) from the current source (or the voltage source) to a predetermined threshold value or more for pulse oscillation. Specifically, the light source control part 5 is one adapted to make the semiconductor laser operate in the quasi-CW oscillation as the pulse oscillation having a predetermined pulse width (e.g., 10 to 50 ns, duty ratio of 5%) and repeated with a predetermined period (e.g., 1 to 5 MHz). In addition, the light source control part 5 is one adapted to change the drive current (drive voltage) from the current source (or the voltage source) at a predetermined frequency with the drive current (drive voltage) set to a value that is for the wavelength sweeping and lower than the threshold value for the pulse oscillation, and thereby change temperature to sweep the oscillation wavelength of the laser light. A modulation signal for modulating the drive current changes in a triangular wave shape, sawtooth wave shape, or sine wave shape, and its frequency is, for example, 1 to 100 Hz.

Figure 7:
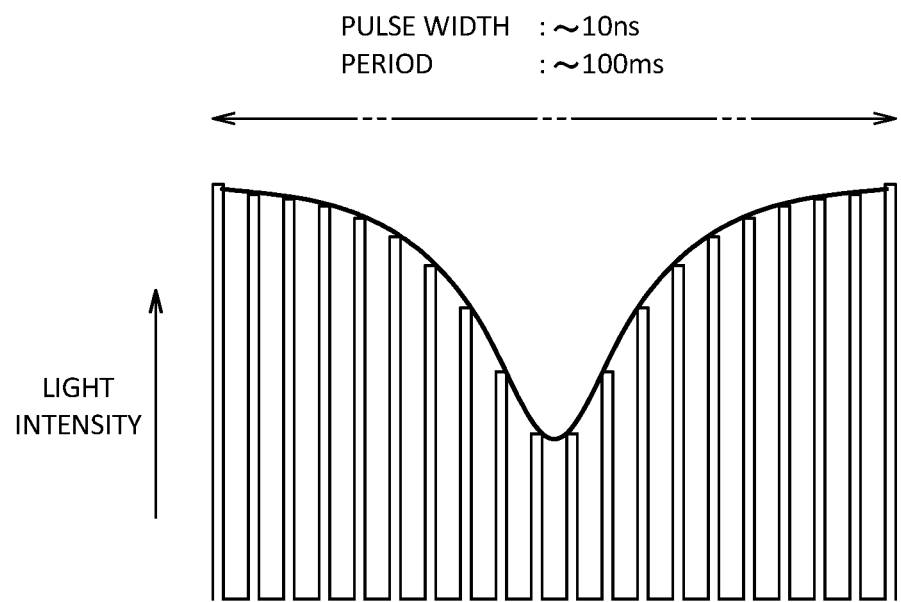
FIG. 7 is a schematic diagram illustrating a measurement principle based on the quasi-CW oscillation.

A light intensity signal obtained by the light detector as a result of making the semiconductor laser operate in quasi-CW oscillation is as illustrated in FIG. 7. As illustrated, an absorption spectrum can be obtained as the entire pulse train. In this case, as the light detector, the use of a high response speed detector such as an MCT is not required, but the use of a low response speed thermal detector such as a thermopile is possible. In addition, as compared with the CW oscillation, the quasi-CW oscillation makes it possible to decrease the power consumption of the light source, facilitate waste heat disposal, and further prolong the life of the light source.

Figure 8:
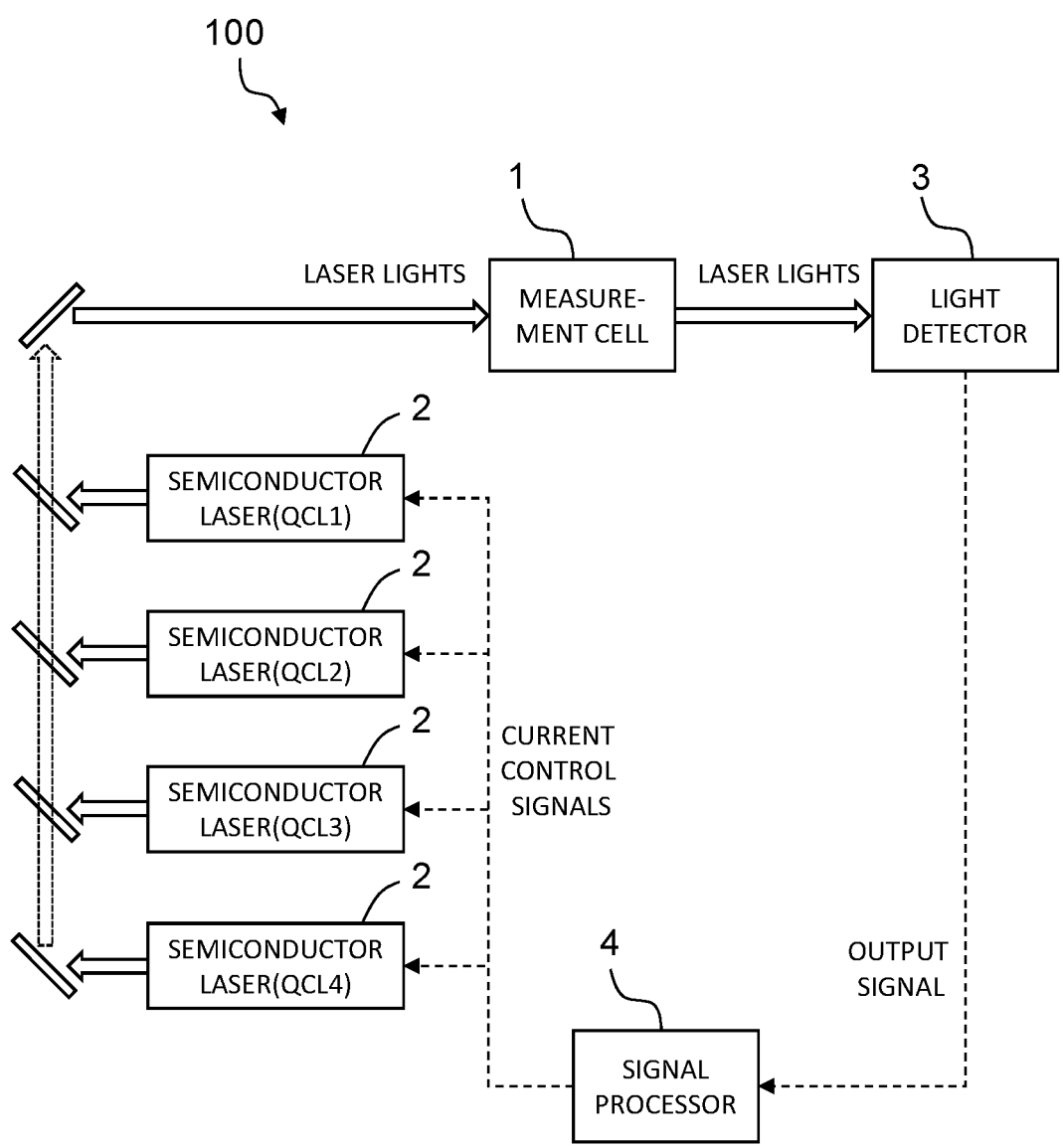
FIG. 8 is an overall schematic diagram of an analysis apparatus according to a variation.
Figure 9:
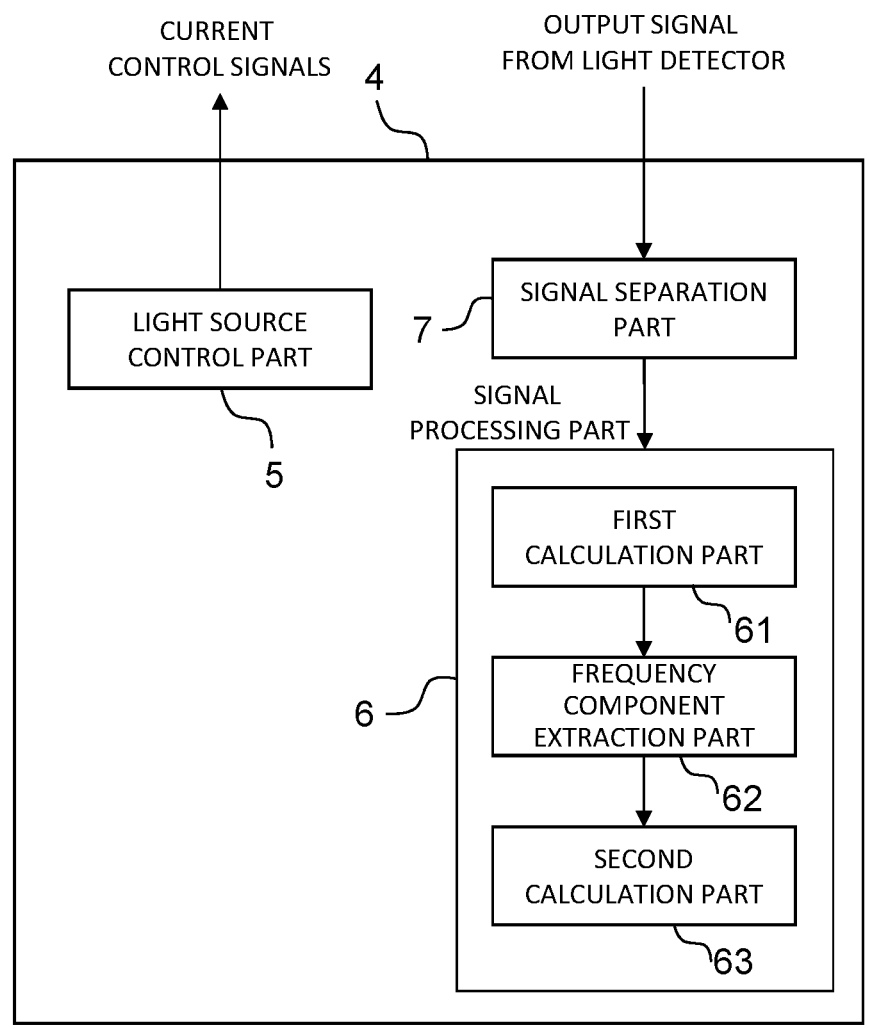
FIG. 9 is a functional block diagram of a signal processor in the variation.

Also, as illustrated in FIG. 8, the analysis apparatus 100 may be one including multiple semiconductor lasers 2 as light sources adapted to irradiate the measurement cell 1 with laser lights. In this case, as illustrated in FIG. 9, a signal processer 4 in the analysis apparatus 100 fulfills functions as a light source control part 5 adapted to control the outputs of the semiconductor lasers 2, a signal separation part 7 adapted to separate signals corresponding to the respective semiconductor lasers 2 from a light intensity signal obtained by the light detector 3, a signal processing part 6 adapted to receive the signals resulting from the separation by the signal separation part 7 and corresponding to the respective semiconductor lasers 2, and perform a calculation process on the values of the signals to calculate the concentrations of measurement target components, and the like.

The light source control part 5 is one adapted to make the respective multiple semiconductor lasers 2 operate in pulse oscillations, and modulate the oscillation wavelengths of the laser lights at a predetermined frequency. Also, the light source control part 5 is adapted to control the multiple semiconductor lasers 2 such that the multiple semiconductor lasers 2 have the oscillation wavelengths corresponding to the respective different measurement target components, and the respective multiple semiconductor lasers 2 operate in the pulse oscillations with mutually different oscillation periods at mutually different oscillation timings.

Specifically, the light source control part 5 outputs current (or voltage) control signals to thereby control the current sources (or the voltage sources) for the respective semiconductor lasers 2. As illustrated in FIG. 3, the light source control part 5 in the present embodiment is one adapted to make the respective semiconductor lasers 2 operate in quasi-CW oscillations as pulse oscillations having a predetermined pulse width (e.g., 10 to 100 nm, duty ratio 5%) and repeated with a predetermined period (e.g., 1 to 5 MHz).

Also, as illustrated in FIG. 6, the light source control part 5 is one adapted to change drive currents (drive voltages) from the current sources (or the voltage sources) at a predetermined frequency, and thereby change temperatures to sweep the oscillation wavelengths of the laser lights. Further, as illustrated in FIG. 3, the oscillation wavelengths of the laser lights are modulated with the peaks of the absorption spectra of the measurement target components as centers. Modulation signals for changing the drive currents are signals that change in a triangular wave shape, sawtooth wave shape, or sine wave shape, and have a frequency of, for example, 1 to 100 Hz. Note that FIG. 6 illustrates an example where a modulation signal changes in a triangular wave shape.

The light intensity signal obtained by the light detector 3 as a result of making one of the semiconductor lasers 2 operate in the quasi-CW oscillation in the above manner is as illustrated in FIG. 7. As illustrated, an absorption spectrum can be obtained as the entire pulse train.

Figure 10:
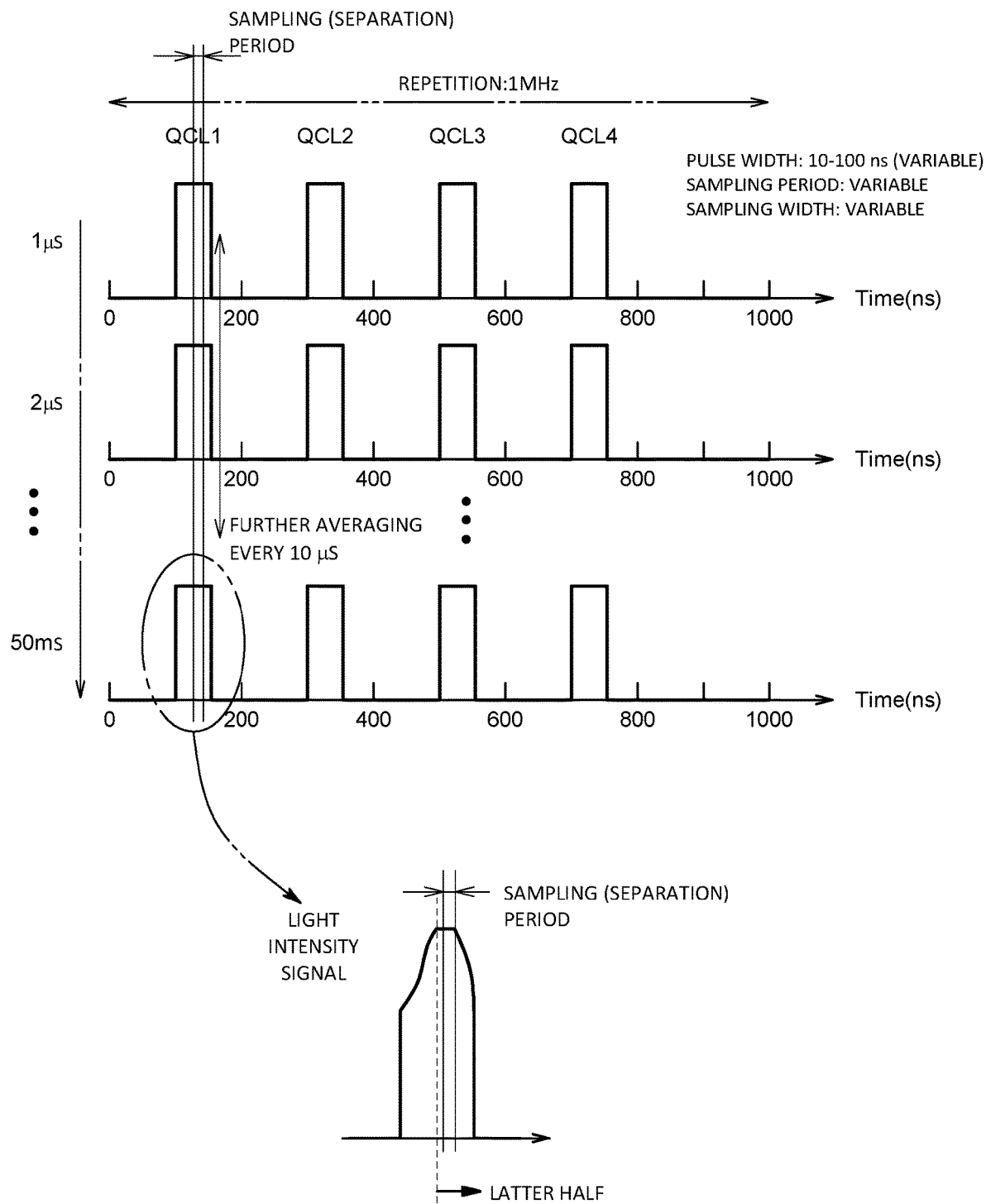
FIG. 10 is a schematic diagram illustrating an example of pulse oscillation timings and light intensity signals of multiple semiconductor lasers in the variation.

Also, the light source control part 5 makes the multiple semiconductor lasers 2 operate in the pulse oscillations at the mutually different timings. Specifically, as illustrated in FIG. 10, the multiple semiconductor lasers 2 sequentially operate in the pulse oscillations, and within one period of pulse oscillation produced by one of the semiconductor lasers 2, one pulses from the other semiconductor lasers 2 are included. That is, between mutually adjacent pulses from one of the semiconductor lasers 2, one pulses from the other semiconductor lasers 2 are included. In this case, pulses from the multiple semiconductor lasers 2 are oscillated so as to prevent the overlap of the pulses.

Figure 11:
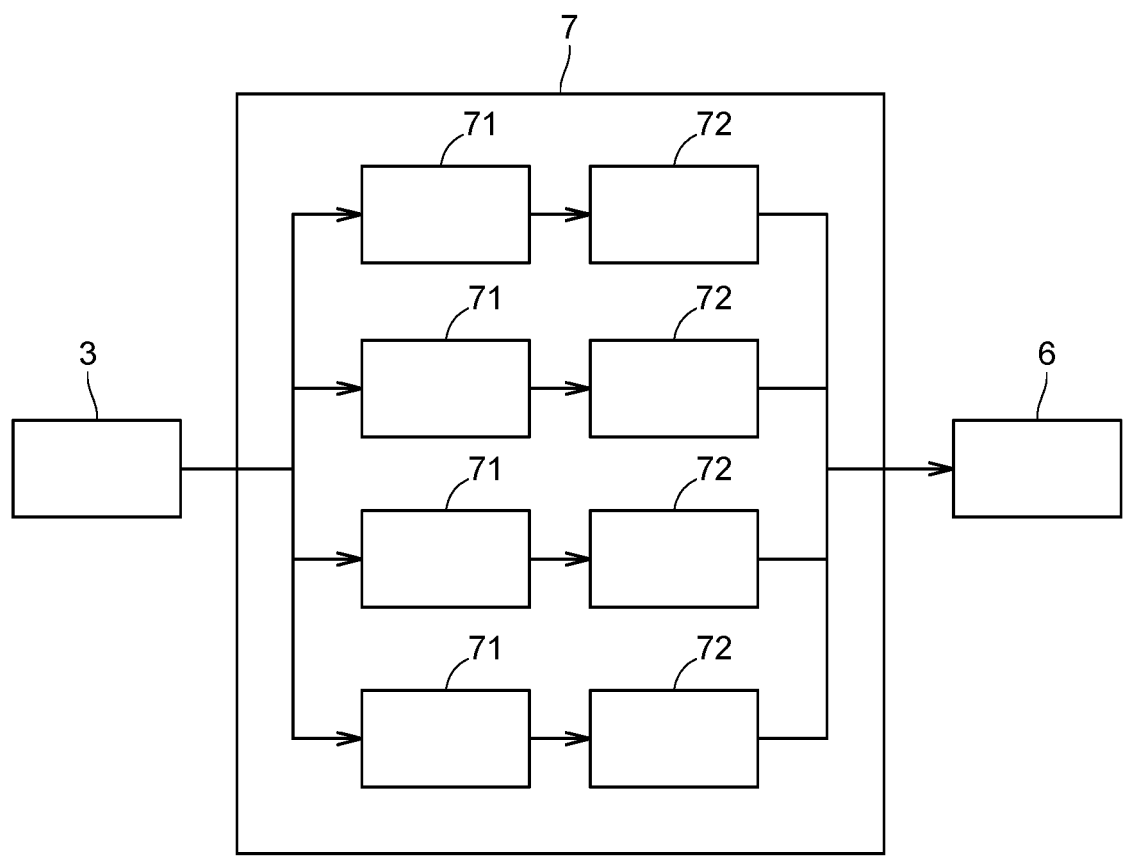
FIG. 11 is a schematic diagram illustrating the configuration of a signal separation part in the variation.

The signal separation part 7 is one adapted to separate the signals corresponding to the respective multiple semiconductor lasers 2 from the light intensity signal obtained by the light detector 3. As illustrated in FIG. 11, the signal separation part 7 in the present embodiment includes: multiple sample-and-hold circuits 71 provided corresponding to the respective multiple semiconductor lasers 2; and AD converters 72 adapted to perform digital conversion of light intensity signals resulting from separation by the sample-and-hold circuits 71.

Each of the sample-and-hold circuits 71 uses a sampling signal synchronized with a current (or a voltage) control signal for a corresponding semiconductor laser 2 to, at timing synchronized with timing at which the semiconductor laser 2 operates in pulse oscillation, separate a signal corresponding to the semiconductor laser 2 from the light intensity signal obtained by the light detector 3, and holds the signal. Note that the sample-and-hold circuit 71 is configured to separate and hold the latter half of the signal, which corresponds to a part of a pulse from the semiconductor laser 2. Since a signal corresponding to the part of a pulse from the semiconductor laser 2 is separated, the pulse width of the pulse does not directly affect wavelength resolution, and therefore a reduction in wavelength resolution can be suppressed without shortening the pulse width. As a result, as compared with a conventional quasi-CW oscillation method, the wavelength resolution can be significantly improved. In addition, since shortening the pulse width to prevent the reduction in wavelength resolution is not required, the technical difficulty required for electronics for driving the semiconductor lasers 2 is reduced, and correspondingly, cost is also reduced.

When a semiconductor laser operates in pulse oscillation, temperature changes to thereby change a wavelength. The degree of such a transient temperature change (wavelength change) becomes smaller toward the latter half of a pulse, and therefore by separating a signal corresponding to the latter half, the wavelength resolution is improved. For this reason, it is preferable that from the light intensity signal obtained by the light detector 3, the signal separation part separates a signal corresponding to the latter half of a pulse from each light source. This configuration makes it possible to significantly improve the wavelength resolution as compared with the conventional quasi-CW oscillation method by relatively widening the pulse width of a pulse (e.g., approximately 100 ns) and setting a sampling position to a time position within the pulse as far back as possible (e.g., 85 to 95 ns after the rise of the pulse). In addition, the sampling is performed within a predetermined time width.

Also, as illustrated in FIG. 10, each of the sample-and-hold circuits 71 separates a signal resulting from averaging over a predetermined sampling period (e.g., 10 ns) in the latter half (e.g., around 80 to 90 ns). Further, in the present embodiment, the signal separation part 7 further averages signals separated from multiple pulse signals from each of the semiconductor lasers 2. For example, signals separated from 10 pulse signals within a period of 5 μs are further averaged. A light absorption spectrum from a signal corresponding to one of the semiconductor lasers 2 and resulting from the separation by the signal separation part 7 is the same as a light absorption spectrum obtained when the one semiconductor laser 2 is made to operate in the quasi-CW oscillation. Since each of the sample-and-hold circuits 71 separates a signal corresponding to a part of a pulse, the AD converters 72 may have even slow processing speed.

The signal processing part 6 calculates the concentrations of the measurement target components corresponding to the respective semiconductor lasers 2 using absorption spectra from signals resulting from the separation by the signal separation part 7 and corresponding to the respective semiconductor lasers 2. Note that the calculation of the concentrations of the measurement target components by the signal processing part 6 is the same as that in the above-described embodiment.

Also, the sample gas is not limited to the exhaust gas but may be the air, liquid, or solid. In that sense, when the measurement target component is not only gas, but liquid or solid, the present invention is applicable as well. In addition, the present invention is applicable not only to the absorbance of light having transmitted through the measurement target but also to absorbance calculation based on reflection.

The light source is also not limited to the semiconductor laser, but may be another type of laser, and any light source may be used as long as the light source is a single wavelength light source having a half width enough to ensure measurement accuracy and can be subjected to wavelength modulation.

Besides, various embodiments may be modified and/or combined without departing from the scope of the present invention.

REFERENCE SIGNS LIST

100: Analysis apparatus
1: Cell
2: Light source (semiconductor laser)
3: Light detector
61: First calculation part
62: Frequency component extraction part
63: Second calculation part

The invention claimed is:

1. An analysis apparatus adapted to analyze a measurement target component contained in a sample that contains one or more interference components, the analysis apparatus comprising:
   a light source adapted to emit reference light having a wavelength that is modulated at a predetermined modulation frequency;
   a light detector adapted to detect intensity of the reference light not transmitted through the sample and intensity of the reference light after transmission through the sample;
   a first calculation part adapted to calculate an intensity ratio logarithm that is a logarithm of a ratio between the intensity of the reference light after transmission through the sample and the intensity of the reference light not transmitted through the sample;
   a frequency component extraction part adapted to, from the intensity ratio logarithm,
   extract a frequency component of n times the modulation frequency,
   wherein n is an integer equal to or more than one, and
   extract mutually different frequency components that are in number equal to or more than a total number of the measurement target component and a number of the one or more interference components to remove influence of interference; and
   a second calculation part adapted to, on a basis of a result of the frequency component extracted by the frequency component extraction part, calculate concentration or absorbance of the measurement target component, wherein the second calculation part is further adapted to calculate the concentration of the measurement target component from which the influence of interference has been removed on a basis of an extraction result of frequency components by the frequency component extraction part.

2. The analysis apparatus according to claim 1, wherein the analysis apparatus
   stores independent frequency components obtained by extracting frequency components from intensity ratio logarithms when the measurement target component and the one or more interference components are independently present or
   stores independent intensity ratio logarithms that are intensity ratio logarithms of the measurement target component and the respective one or more interference components per unit concentration, and
   the second calculation part is adapted to calculate the concentration of the measurement target component on a basis of a result of the extraction of the respective frequency components by the frequency component extraction part and the independent frequency components or the independent intensity ratio logarithms.

3. The analysis apparatus according to claim 2, wherein the second calculation part is adapted to calculate the concentration of the measurement target component by solving simultaneous equations that include as parameters the result of the extraction of the respective frequency components by the frequency component extraction part, the independent frequency components or the independent intensity ratio logarithms of the measurement target component and the respective interference components, and concentrations of the measurement target component and the respective one or more interference components.

4. The analysis apparatus according to claim 3, wherein the second calculation part is adapted to calculate the concentration of the measurement target component with use of a least squares method, wherein a number of unknowns of the simultaneous equations is greater than a sum of the number of the measurement target component and the number of the one or more interference components.

5. The analysis apparatus according to claim 2, wherein the number of the one or more interference components is a largest number of gas components assumed to be contained in the sample.

6. The analysis apparatus according to claim 1, wherein the frequency component extraction part is adapted to extract the frequency component or the frequency components by performing lock-in detection at the frequency n times the modulation frequency.

7. The analysis apparatus according to claim 1, wherein the first calculation part is adapted to calculate the intensity ratio logarithm by obtaining the ratio between the intensity of the reference light after transmission through the sample and the intensity of the reference light not transmitted through the sample, and obtaining a logarithm of the ratio.

8. The analysis apparatus according to claim 1, wherein the first calculation part is adapted to calculate the intensity ratio logarithm by obtaining a logarithm of the intensity of the reference light after transmission through the sample, obtaining a logarithm of the intensity of the reference light not transmitted through the sample, and subtracting the logarithm of the intensity of the reference light not transmitted through the sample from the logarithm of the intensity of the reference light after transmission through the sample.

9. The analysis apparatus according to claim 1, wherein the sample is a sample gas,
the light source is a semiconductor laser adapted to emit the reference light modulated in a wavelength range including a peak wavelength of a light absorption spectrum of the measurement target component,
the analysis apparatus further comprises a cell into which the sample gas is introduced,
the cell is irradiated with the reference light emitted from the semiconductor laser, and
the light detector is arranged in a light path of the measurement target light having transmitted through the cell.

10. The analysis apparatus according to claim 1, further comprising
a light source control part adapted to make the light source operate in quasi-continuous-wave oscillation, and generate a temperature change based on current modulation to sweep an oscillation wavelength.

11. The analysis apparatus according to claim 10, further comprising
a signal separation part adapted to, from a light intensity signal obtained by the light detector, separate a signal corresponding to a part of a pulse from the light source.

12. The analysis apparatus according to claim 11, wherein the signal separation part is adapted to separate a signal corresponding to a latter half of the pulse of the light source.

13. A non-transitory computer-readable medium storing a program for an analysis apparatus, the program being applied to an analysis apparatus that in order to analyze a measurement target component contained in a sample that contains one or more interference components, comprises a light source adapted to emit reference light having a wavelength that is modulated at a predetermined modulation frequency, and a light detector adapted to detect intensity of the reference light not transmitted through the sample and intensity of the reference light after transmission through the sample,
the program instructing the analysis apparatus to fulfill functions as:
a first calculation part adapted to calculate an intensity ratio logarithm that is a logarithm of a ratio between the intensity of the reference light after transmission through the sample and the intensity of the reference light not transmitted through the sample;
a frequency component extraction part adapted to, from the intensity ratio logarithm,
extract a frequency component of n times the modulation frequency,
wherein n is an integer equal to or more than one, and
extract mutually different frequency components that are in number equal to or more than a total number of the measurement target component and a number of the one or more interference components to remove influence of interference; and
a second calculation part adapted to, on a basis of a result of the frequency component extracted by the frequency component extraction part, calculate concentration or absorbance of the measurement target component, wherein the second calculation part is further adapted to calculate the concentration of the measurement target component from which the influence of interference has been removed based on an extraction result of frequency components by the frequency component extraction part.

14. An analysis method adapted to analyze a measurement target component contained in a sample that contains one or more interference components, the analysis method comprising:
emitting reference light having a wavelength that is modulated at a predetermined modulation frequency;
detecting intensity of the reference light not transmitted through the sample and intensity of the reference light after transmission through the sample;
calculating an intensity ratio logarithm that is a logarithm of a ratio between the intensity of the reference light after transmission through the sample and the intensity of the reference light not transmitted through the sample;
from the intensity ratio logarithm,
extracting a frequency component of n times the modulation frequency, wherein n is an integer equal to or more than one, and
extracting mutually different frequency components that are in number equal to or more than a total number of the measurement target component and a number of the one or more interference components to remove influence of interference; and
on a basis of a result of the extraction of the frequency component, calculating concentration or absorbance of the measurement target component, wherein the concentration of the measurement target component is further calculated on a basis of a result of the extraction of the mutually different frequency components.

15. The analysis method according to claim 14 further comprising:
extracting independent frequency components that are frequency components from intensity ratio logarithms when the measurement target component and the one or more interference components are independently present, or measuring independent intensity ratio logarithms that are intensity ratio logarithms of the measurement target component and the one or more interference components per unit concentration, and
calculating the concentration of the measurement target component on a basis of a result of the extraction of the respective frequency components obtained from the sample and the independent frequency components or the independent intensity ratio logarithms.

16. An analysis apparatus adapted to analyze a measurement target component contained in a sample that contains one or more interference components, the analysis apparatus comprising:
a light source adapted to emit reference light having a wavelength that is modulated at a predetermined modulation frequency;

a light detector adapted to detect intensity of the reference light not transmitted through the sample and intensity of the reference light after transmission through the sample;

a first calculation part adapted to calculate an intensity ratio logarithm that is a logarithm of a ratio between the intensity of the reference light after transmission through the sample and the intensity of the reference light not transmitted through the sample;

a frequency component extraction part adapted to, from the intensity ratio logarithm, extract a frequency component of n times the modulation frequency, wherein n is an integer equal to or more than one;

extract mutually different frequency components that are in number equal to or more than a total number of the measurement target component and a number of the one or more interference components;

memory adapted to store independent frequency components obtained by extracting frequency components from intensity ratio logarithms when the measurement target component and the one or more interference components are independently present, or store independent intensity ratio logarithms that are intensity ratio logarithms of the measurement target component and the one or more interference components per unit concentration; and a second calculation part adapted to, calculate concentration or absorbance of the measurement target component on a basis of a result of the frequency component extracted by the frequency component extraction part, and calculate the concentration of the measurement target component on a basis of a result of the extraction of the respective frequency components by the frequency component extraction part and the independent frequency components or the independent intensity ratio logarithms.

17. The analysis apparatus according to claim 16, wherein the second calculation part is adapted to calculate the concentration of the measurement target component by solving simultaneous equations that include as parameters the result of the extraction of the respective frequency components by the frequency component extraction part, the independent frequency components or the independent intensity ratio logarithms of the measurement target component and the respective interference components, and concentrations of the measurement target component and the one or more interference components.

18. The analysis apparatus according to claim 17, wherein the second calculation part is adapted to calculate the concentration of the measurement target component with use of a least squares method, wherein a number of unknowns of the simultaneous equations is greater than a sum of the number of the measurement target component and the number of the one or more interference components.

19. The analysis apparatus according to claim 16, wherein the number of the one or more interference components is a largest number of gas components assumed to be contained in the sample.

20. The analysis apparatus according to claim 16, wherein the frequency component extraction part is adapted to extract the frequency component or the frequency components by performing lock-in detection at the frequency n times the modulation frequency.

* * * * *